(12) United States Patent
Mertens et al.

(10) Patent No.: US 7,518,026 B2
(45) Date of Patent: Apr. 14, 2009

(54) CATALYST AND PROCESS FOR THE CONVERSION OF OXYGENATES TO OLEFINS

(75) Inventors: Machteld M. Mertens, Boortmeerbeek (BE); Marcel J. Janssen, Kessel-Lo (BE); Yun-feng Chang, Houston, TX (US); Stephen N. Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 982 days.

(21) Appl. No.: 10/956,423

(22) Filed: Oct. 1, 2004

(65) Prior Publication Data

US 2006/0074266 A1   Apr. 6, 2006

(51) Int. Cl.
*C07C 1/20* (2006.01)
(52) U.S. Cl. ............... 585/638; 585/639; 585/640; 585/326; 585/327; 585/329
(58) Field of Classification Search ................. 208/638, 208/639, 640, 326, 327, 329
See application file for complete search history.

(56) References Cited

U.S. PATENT DOCUMENTS

| | | | |
|---|---|---|---|
| 4,440,871 A | 4/1984 | Lok et al. | 502/214 |
| 5,279,810 A | 1/1994 | Calabro | 423/701 |
| 6,334,994 B1 | 1/2002 | Wendelbo et al. | 423/718 |
| 6,531,639 B1 | 3/2003 | Fung et al. | 585/638 |
| 6,953,767 B2* | 10/2005 | Janssen et al. | 502/214 |
| 7,067,095 B1* | 6/2006 | Mertens | 423/306 |
| 7,094,389 B2* | 8/2006 | Cao et al. | 423/706 |

FOREIGN PATENT DOCUMENTS

WO   WO 02/70407   9/2002
WO   WO 03/106341   12/2003

OTHER PUBLICATIONS

*Atlas of Zeolite Framework Types*, 5th edition, Elsevier, London, England, pp. 3-18, 24, 96 and 97 (2001).
J. Chen et al. in Journal of Physical Chemistry, "Catalysts and Their Bronsted Acid Sites", vol. 98, pp. 10216-10224 (1994).
A. M. Prakash et al. in Journal of the Chemical Society, Faraday Transactions, "Synthesis of SAPO-34: High Silicon Incorporation in the Presence of Morpholine as Template", vol. 90(15), pp. 2291-2296 (1994).
Yan Xu et al. in Journal of the Chemical Society, Faraday Transactions, "The Synthesis of SAPO-34 and CoSAPO-34 from a Triethylamine-Hydrofluoric Acid-Water System", vol. 86(2), pp. 425-429 (1990).
M. M. J. Tracey et al. in Proceedings of the Royal Chemical Society, London, A, "A General Recursion Method for Calculating Diffracted Intensities from Crystals Containing Planar Faults", [1991], vol. 433, pp. 499-520).
J. Chen et al. in Catalysis Letters, "Silicoaluminophosphate No. Eighteen (SAPO-18): a New Microporous Solid Acid Catalyst", vol. 28, pp. 241-248 (1994).
E.B. Keller et al. in Solid State Ionics 43, "Synthesis, structures of $ALPO_4$-C and $ALPO_4$-D and their Topotactic Transformation", (1990) pp. 93-102.
L. Canesson et al. in Microporous and Mesoporous Materials 26, "Synthesis and Characterization of Cobalt-Containing Hydrated Aluminophosphate Molecular Sieves $CoAPO_4$-H3", (1998) pp. 117-131.
B. Duncan et al. in Bull. Soc. Chim. Fr., "Template-Free Synthesis of the Aluminophosphates H1 through H4", (1992), 129, pp. 98-110.
K. Kunii et al. in Microporous and Mesoporous Materials 50, "Template-Free Synthesis and Adsorption Properties of Microporous Crystal $ALPO_4$-H3", (2001) pp. 181-185.
F. d'Yvoire, "Etude des phosphates d'aluminium et de fer trivalents. 1. L'orthophosphate neutre d'aluminium", Bull. Soc. Chim. France (1961) 1762 (translated by Ralph McElroy Translation Company).

* cited by examiner

*Primary Examiner*—Tam M Nguyen

(57) ABSTRACT

A catalyst composition for use in the conversion of oxygenates to olefins comprises a first crystalline silicoaluminophosphate molecular sieve comprising at least one intergrown form of an AEI structure type material and a CHA structure type material, and a second crystalline material different from said first molecular sieve and resulting from dehydration of an aluminophosphate or silicoaluminophosphate hydrate.

3 Claims, 2 Drawing Sheets

CATALYST AND PROCESS FOR THE CONVERSION OF OXYGENATES TO OLEFINS

FIELD OF INVENTION

This invention relates to a catalyst and process for the conversion of oxygenates, particularly methanol, to olefins, particularly ethylene and propylene.

BACKGROUND OF INVENTION

Light olefins, such as ethylene, propylene, butylenes and mixtures thereof, serve as feeds for the production of numerous important chemicals and polymers. Typically, $C_2$-$C_4$ light olefins are produced by cracking petroleum refinery streams, such as $C_3$+ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$-$C_4$ alkanols, especially methanol and ethanol; $C_2$-$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as an economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Crystalline molecular sieves have a 3-dimensional, four-connected framework structure of corner-sharing [$TO_4$] tetrahedra, where T is any tetrahedrally coordinated cation. Among the known forms of molecular sieve are aluminosilicates, which contain a three-dimensional microporous crystal framework structure of [$SiO_4$] and [$AlO_4$] corner sharing tetrahedral units silicoaluminophosphates (SAPOs), in which the framework structure is composed of [$SiO_4$], [$AlO_4$] and [$PO_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types*, 5th edition, Elsevier, London, England (2001), which is herein fully incorporated by reference.

Among the molecular sieves that have been investigated for use as oxygenate conversion catalysts, materials having the framework type of the zeolitic mineral chabazite (CHA) have shown particular promise. For example, SAPO-34 is a crystalline silicoaluminophosphate molecular sieve of the CHA framework type and has been found to exhibit relatively high product selectivity to ethylene and propylene, and low product selectivity to paraffins and olefins with four or more carbon atoms.

The preparation and characterization of SAPO-34 have been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", Vol. 28, pp. 241-248 (1994); A. M. Prakash et al. in "Journal of the Chemical Society, Faraday Transactions" Vol. 90(15), pp. 2291-2296 (1994); Yan Xu et al. in "Journal of the Chemical Society, Faraday Transactions" Vol. 86(2), pp. 425-429 (1990).

Regular crystalline molecular sieves, such as the CHA framework type materials, are built from structurally invariant building units, called Periodic Building Units, and are periodically ordered in three dimensions. Disordered structures showing periodic ordering in less than three dimensions are, however, also known. One such disordered structure is a disordered planar intergrowth in which the building units from more than one framework type, e.g., both AEI and CHA, are present. One well-known method for characterizing crystalline materials with planar faults is DIFFaX, a computer program based on a mathematical model for calculating intensities from crystals containing planar faults (see M. M. J. Tracey et al., Proceedings of the Royal Chemical Society, London, A [1991], Vol. 433, pp. 499-520).

International Patent Publication No. WO 02/70407, published Sep. 12, 2002 and incorporated herein by reference, discloses a silicoaluminophosphate molecular sieve, now designated EMM-2, comprising at least one intergrown form of molecular sieves having AEI and CHA framework types, wherein said intergrown form has an AEI/CHA ratio of from about 5/95 to 40/60 as determined by DIFFaX analysis, using the powder X-ray diffraction pattern of a calcined sample of said silicoaluminophosphate molecular sieve. EMM-2 has been found to exhibit significant activity and selectivity as a catalyst for the production of light olefins from methanol (MTO).

U.S. Pat. No. 6,334,994, incorporated herein by reference, discloses a silicoaluminophosphate molecular sieve, referred to as RUW-19, which is also said to be an AEI/CHA mixed phase composition. In particular, RUW-19 is reported as having peaks characteristic of both AEI and CHA structure type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. DIFFaX analysis of the X-ray diffraction pattern of RUW-19 as produced in Examples 1, 2 and 3 of U.S. Pat. No. 6,334,994 indicates that these materials are characterized by single intergrown forms of AEI and CHA structure type molecular sieves with AEI/CHA ratios of about 60/40, 65/35 and 70/30. RUW-19 is reported to be active as a catalyst in the production of light olefins from methanol (MTO).

Study of the synthesis of EMM-2 has shown that the crystallization process to produce such AEI/CHA intergrowths proceeds through the formation of a (silico)aluminophosphate hydrate precursor, such as ALPO-H3 and/or variscite and/or metavariscite, during heat-up of the mixture, followed by dissolution of the precursor as the intergrown molecular sieve nucleates. Unless the temperature and time of nucleation and the amount of directing agent in the synthesis mixture are sufficient, it has been found that significant quantities of the hydrate can be present in the as-synthesized product.

On heating (silico)aluminophosphate hydrates undergo dehydration to produce other crystalline phases, such as phosphocristobolite, phosphotridymite, ALPO-A, ALPO-C, ALPO-D, ALPO-E, dehydrated variscite and dehydrated metavariscite. For example, ALPO-H3 forms ALPO-C on dehydration. ALPO-C has the APC structure having two sets channels defined by eight-membered rings of tetrahedrally coordinated atoms with pore sizes of about 0.34×0.37 nm and about 0.29×0.57 nm. In contrast, both CHA and AEI structure type materials have a pore size of about 0.38×0.38 nm. Thus it was believed that the presence of such impurity phases would be deleterious to the catalytic properties of the intergrowth and so the synthesis process should be closely controlled to avoid the production of these impurities.

Surprisingly, it has now been found that a catalyst composition comprising an AEI/CHA intergrowth exhibits excellent selectivity to ethylene and propylene in oxygenate conversion even if the catalyst composition also contains one or more additional crystalline phases resulting from the dehydration of (silico)aluminophosphate hydrate(s) produced during synthesis of the intergrowth. This finding significantly simplifies the synthesis of AEI/CHA intergrowths by, for example, allowing crystallization temperature and/or time to be reduced and allowing the amount of expensive directing agent required to synthesize the intergrowth to be reduced.

Aluminophosphate hydrates, such as ALPO-H3, and their transformation on heating to other crystalline phases, such as ALPO-C, are disclosed in, for example, F. d'Yvoire, "Etude des phosphates d'aluminium et de fer trivalents. 1. L'orthophosphate neutre d'aluminium", Bull. Soc. Chim. France (1961) 1762; E. B. Keller et al., "Synthesis, structures of $ALPO_4$-C and $ALPO_4$-D and their topotactic transformation", Solid State Ionics 43 (1990) 93-102; L. Canesson et al., "Synthesis and characterization of cobalt-containing hydrated aluminophosphate molecular sieves $CoAPO_4$-H3", Microporous and Mesoporous Materials 25 (1998) 117-131; B. Duncan et al., "Template-free synthesis of the aluminophosphates H1 through H4", Bull. Soc. Chim. Fr. (1992), 129, 98-110 and K. Kunii et al., "Template-free synthesis and adsorption properties of microporous crstal $ALPO_4$-H3", Microporous and Mesoporous Materials 50 (2001) 181-185.

U.S. Pat. No. 6,531,639 discloses a method of making an olefin product from an oxygenate-containing feedstock by contacting the feedstock with a non-zeolite catalyst at an oxygenate partial pressure of greater than 20 psia, a weight hourly space velocity of greater than 2 $hr^{-1}$, an average gas superficial velocity of greater than 1 meter per second, and an oxygenate proportion index of at least 0.5. The catalyst employed is a silicoaluminophosphate (SAPO) molecular sieve selected from SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal-containing forms, mixtures and intergrowths thereof. In addition, further olefin-forming molecular sieve materials can be included as a part of the SAPO catalyst composition or as separate molecular sieve catalysts in admixture with the SAPO catalyst if desired. Examples of suitable small pore molecular sieves are said to include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO structure type materials, whereas examples of suitable medium pore molecular sieves are said to include MFI, MEL, MTW, EUO, MTT, HEU, FER, AFO, AEL and TON structure type materials.

SUMMARY

In one aspect, the invention resides in a catalyst composition for use in the conversion of oxygenates to olefins comprising a first crystalline silicoaluminophosphate molecular sieve comprising at least one intergrown form of an AEI structure type material and a CHA structure type material, and a second crystalline material different from said first molecular sieve and resulting from dehydration of an aluminophosphate or silicoaluminophosphate hydrate.

Conveniently, said second crystalline material is present in an amount up to 40%, for example between about 3% and about 30%, such as between about 5% and about 15%, by weight of the total weight of said first crystalline silicoaluminophosphate molecular sieve and said second crystalline material.

Conveniently, said second crystalline material comprises one or more of phosphocristobolite, phosphotridymite, ALPO-A, ALPO-C, ALPO-D, ALPO-E, dehydrated variscite and dehydrated metavariscite, and preferably comprises one or more of ALPO-C, dehydrated variscite and dehydrated metavariscite.

In one embodiment, said at least one intergrown form has an AEI/CHA ratio of from about 5/95 to about 40/60, for example from about 10/90 to about 30/70, such as from about 15/85 to about 20/80, as determined by DIFFaX analysis. In a further embodiment, the first silicoaluminophosphate molecular sieve comprises first and second intergrown forms each of an AEI framework type material and a CHA framework type material, the first intergrown form having an AEI/CHA ratio of from about 5/95 to about 40/60 as determined by DIFFaX analysis, and the second intergrown form having a different AEI/CHA ratio from said first intergrown form, such as an AEI/CHA ratio of about 50/50 as determined by DIFFaX analysis.

In a further aspect, the invention resides in a catalyst composition for use in the conversion of oxygenates to olefins comprising a silicoaluminophosphate first molecular sieve comprising at least one intergrown form of a CHA structure type material and an AEI structure type material, wherein said at least one intergrown form has an AEI/CHA ratio of from about 5/95 to about 40/60 as determined by DIFFaX analysis, and a second molecular sieve having an APC structure type.

In yet a further aspect, the invention resides in a method of producing a crystalline silicoaluminophosphate molecular sieve comprising at least one intergrown form of an AEI structure type material and a CHA structure type material, the method comprising:

(a) preparing a mixture comprising sources of silicon, aluminum and phosphorus and further comprising at least one organic directing agent;

(b) subjecting said mixture to conditions sufficient to form an aluminophosphate or silicoaluminophosphate hydrate precursor of said molecular sieve;

(c) subjecting said mixture to conditions sufficient to convert said precursor to said molecular sieve; and (d) prior to completion of (c), recovering a product comprising said precursor and said molecular sieve.

Conveniently, the method further comprises calcining the product recovered in (d) and formulating said product into a catalyst composition.

In still a further aspect, the invention resides in a process for converting an oxygenate-containing feedstock to a product comprising olefins, the process comprising contacting the feedstock under oxygenate to olefin conversion conditions with a catalyst composition as described herein.

As used herein, the term "aluminophosphate or silicoaluminophosphate hydrate" means an aluminophosphate or silicoaluminophosphate where water is part of the crystal framework, as opposed to what is often referred to as "hydrated molecular sieves", in which water is not part of the crystal structure, but is extra-framework material. The hydrated aluminophosphate structures contain some or all of the structural aluminum in octahedral coordination and water is part of their structure. For example, variscite and metavariscite, both compositionally $AlPO_4 \cdot 2H_2O$, contain 4 and 8-member ring building units where the aluminum is in octohedral coordination. AlPO-H3 has the composition $AlPO_4 \cdot 1.5H_2O$ and both octahedral and tetrahedral aluminum is present in the structure.

DETAILED DESCRIPTION OF THE EMBODIMENTS

Figure 1A:
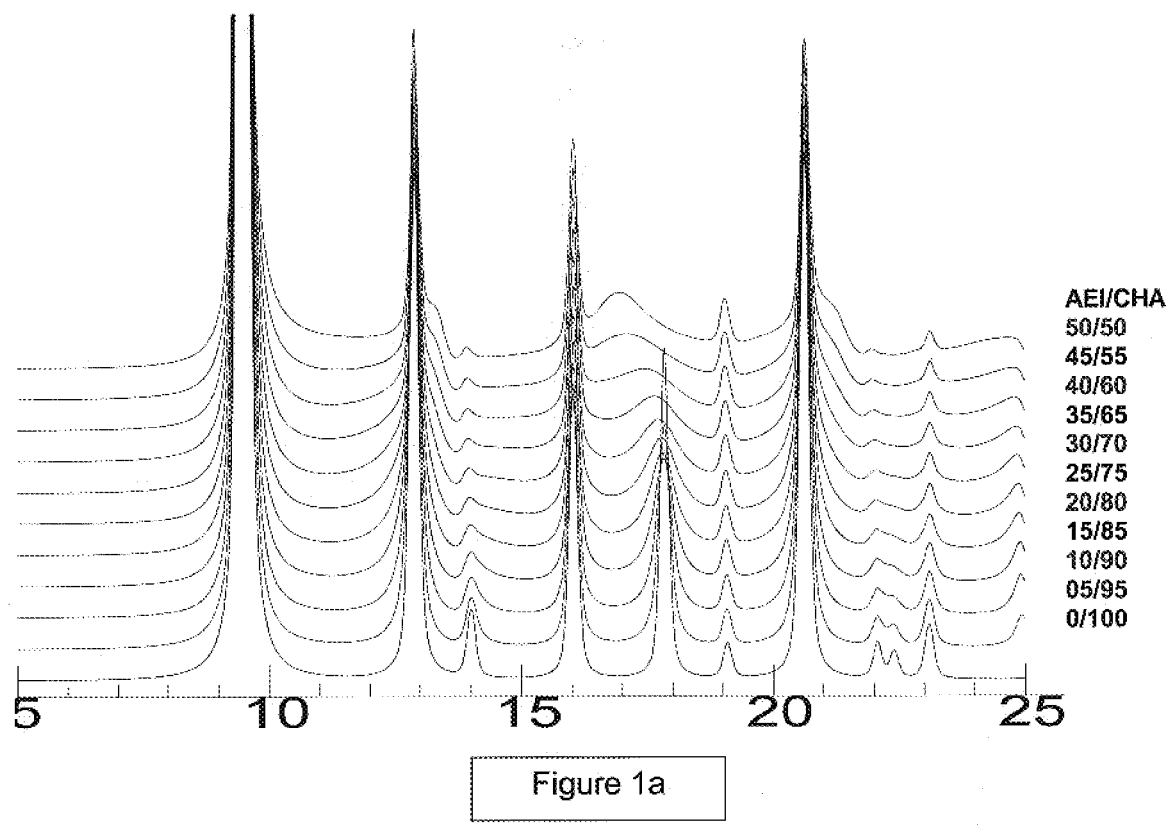
FIGS. 1a and 1b are DIFFaX simulated diffraction patterns for intergrown AEI/CHA phases having varying AEI/CHA ratios.

The present invention relates to the composition and synthesis of a catalyst useful in the conversion of an oxygenate-containing feedstock, such as methanol, to a product comprising olefins, such as ethylene and propylene. In particular, the catalyst composition comprises a crystalline silicoaluminophosphate molecular sieve comprising at least one intergrown form of an AEI structure type material and a CHA structure type material, and a further crystalline phase different from said intergrown form and resulting from dehydration of an aluminophosphate or silicoaluminophosphate hydrate.

According to the invention, it has been found that the synthesis of AEI/CHA intergrowths proceeds through the formation, and subsequent dissolution, of certain (silico)aluminophosphate hydrate precursors, such as ALPO-H3, variscite and/or metavariscite. Thus, unless the synthesis proceeds to completion, significant amounts of these hydrate precursors can be present in the as-synthesized product. On calcination, such as, for example, to remove the organic directing agent used in the intergrowth synthesis, the precursors are dehydrated to produce a further crystalline phase different from AEI/CHA intergrown phase, such as ALPO-C, dehydrated variscite and/or dehydrated metavariscite.

Surprisingly, despite the presence of this further crystalline phase, a catalyst composition produced from the resulting intergrowth exhibits excellent selectivity to ethylene and propylene when used in the conversion of oxygenates, such as methanol. This finding significantly simplifies the synthesis of AEI/CHA intergrowths by, for example, allowing crystallization temperature and/or time to be reduced and allowing the amount of expensive directing agent required to synthesize the intergrowth to be reduced.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

The intergrown silicoaluminophosphate molecular sieves described herein are disordered planar intergrowth of end-member structures AEI and CHA. For AEI and CHA structure types, the Periodic Building Unit is a double six ring layer. There are two types of layers "a" and "b", which are topologically identical except "b" is the mirror image of "a". When layers of the same type stack on top of one another, i.e. . . . aaa . . . or . . . bbb . . . , the framework type CHA is generated. When layers "a" and "b" alternate, e.g., . . . abab . . . , a different framework type, namely AEI, is generated. The intergrown molecular sieves described herein comprise stackings of layers "a" and "b" containing regions of CHA framework type and regions of AEI framework type. Each change of CHA to AEI framework type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543-550.

Figure 1B:
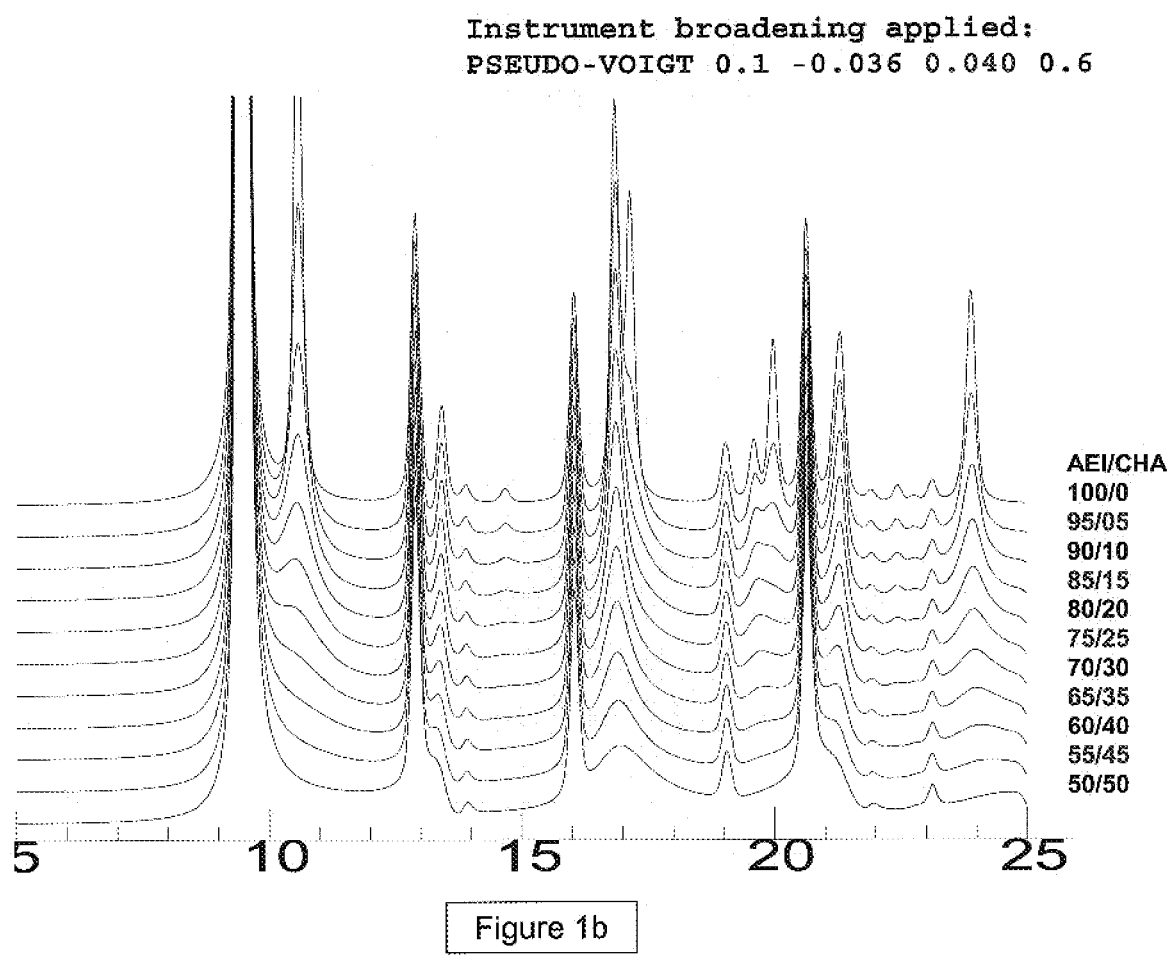

FIGS. 1a and 1b show the simulated diffraction patterns obtained for intergrowths of a CHA framework type molecular sieve with an AEI framework type molecular sieve having various AEI/CHA ratios. FIG. 1a shows the diffraction patterns in the 15 to 35 (2θ) range simulated by DIFFaX for intergrown phases with AEI/CHA ratios of 0/100 (CHA end-member), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50). FIG. 1b shows the diffraction patterns in the range of 5 to 20 (2θ) simulated by DIFFaX for intergrown phases with AEI/CHA ratios of 0/100 (CHA end-member), 10/90 (AEI/CHA=0.11), 20/80 (AEI/CHA=0,25), 50/50 (AEI/CHA=1.0), 70/30 (AEI/CHA=2.33), 80/20 (AEI/CHA=4.0), 100/0 (AEI end-member). All XRD diffraction patterns are normalized to the highest peak of the entire set of simulated patterns, i.e. the peak at about 9.5 degrees 2θ for pure CHA (AEI/CHA ratio of 0/100). Such normalization of intensity values allows a quantitative determination of mixtures of intergrowths As the ratio of AEI increases relative to CHA in the intergrown phase, one can observe a decrease in intensity of certain peaks, for example, the peak at about 2θ=25.0 and an increase in intensity of other peaks, for example the peak at about 2θ=17.05 and the shoulder at 2θ=21.2. Intergrown phases with AEI/CHA ratios of 50/50 and above (AEI/CHA≧1.0) show a broad feature centered at about 16.9 (2θ).

In a preferred embodiment, the intergrown silicoaluminophosphate molecular sieve employed in the catalyst composition of the invention is at least one intergrowth of an AEI framework type and a CHA framework type, wherein said at least one intergrowth has an AEI/CHA ratio of from about 5/95 to about 40/60, for example from about 10/90 to about 30/70, such as from about 15/85 to about 20/80, as determined by DIFFaX analysis. Such a CHA-rich intergrowth is characterized by a powder XRD diffraction pattern (obtained from a sample after calcination and without rehydration after calcination) having at least the reflections in the 5 to 25 (2θ) range as shown in Table 1 below:

TABLE 1

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0 |

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not extra-framework material such as water or template in the cavities. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. Recording under the same conditions immediately after removal of the Mylar foil will also provide a diffraction pattern suitable for use in DIFFaX analysis.

In an alternative embodiment, the intergrown silicoaluminophosphate molecular sieve employed in the catalyst composition of the invention comprises a plurality of intergrown forms of the CHA and AEI framework types, typically with a first intergrown form having an AEI/CHA ratio of from about 5/95 to about 40/60, as determined by DIFFaX analysis, and a second intergrown form having a different AEI/CHA ratio from said first intergrown form. The second intergrown form typically has an AEI/CHA ratio of about 30/70 to about 55/45, such as about 50/50, as determined by DIFFaX analaysis, in which case the XRD diffraction pattern exhibits a broad feature centered at about 16.9 (2θ) in addition to the reflection peaks listed in Table 1.

Preferably, the CHA framework type molecular sieve in the intergrowth of the invention is SAPO-34 and the AEI framework type molecular sieve is selected from SAPO-18, ALPO-18 and mixtures thereof. In addition, the intergrown silicoaluminophosphate preferably has a framework silica to alumina molar ratio (Si/Al$_2$) greater than 0.16 and less than 0.19, such as from about 0.165 to about 0.185, for example about 0.18. The framework silica to alumina molar ratio is conveniently determined by NMR analysis.

Silicoaluminophosphate molecular sieves comprising CHA/AEI intergrowths may conveniently be prepared by a process that comprises:

a) combining reactive sources of silicon, phosphorus and aluminum with an organic structure directing agent (template) to form a mixture having a molar composition within the following ranges:

P$_2$O$_5$:Al$_2$O$_3$ from about 0.6 to about 1.2,
SiO$_2$:Al$_2$O$_3$ from about 0.005 to about 0.35,
H$_2$O:Al$_2$O$_3$ from about 10 to about 50;

b) mixing and heating the mixture (a) continuously to a crystallization temperature, such as between about 100° C. and about 250° C., typically between about 140° C. and about 180° C., preferably between about 150° C. and about 170° C.;

c) maintaining the mixture at the crystallization for a period of time of from 2 to 150 hours; such as from about 5 to about 100 hours, for example from about 10 to about 50 hours; and (d) recovering a crystalline product containing the desired molecular sieve.

The reactive source of silicon used in the above mixture may be a silicate, e.g., fumed silica, such as Aerosil (available from Degussa), a tetraalkyl orthosilicate, or an aqueous colloidal suspension of silica, for example that sold by E.I. du Pont de Nemours under the tradename Ludox. The reactive source of phosphorus used in the above mixture is conveniently phosphoric acid. Examples of suitable reactive aluminum sources include hydrated aluminum oxides such as boehmite and pseudoboehmite. Preferably, pseudoboehmite is used. The organic structure directing agent conveniently includes a tetraethyl ammonium compound, such as tetraethyl ammonium hydroxide (TEAOH), tetraethyl ammonium phosphate, tetraethyl ammonium fluoride, tetraethyl ammonium bromide, tetraethyl ammonium chloride or tetraethyl ammonium acetate. Typically, the directing agent includes tetraethyl ammonium hydroxide. In some cases, more than one organic structure directing agent may be employed, such as a combination of a tetraethyl ammonium compound and dipropylamine.

As a result of the synthesis process, the crystalline product recovered in step (d) contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system.

The synthesis process to produce the AEI/CHA intergrowth proceeds through the formation of a (silico)aluminophosphate hydrate precursor, such as ALPO-H3 and/or variscite and/or metavariscite, during heat-up of the mixture, followed by dissolution of the precursor as the intergrown molecular sieve nucleates. Unless the temperature and time of nucleation and the amount of directing agent in the synthesis mixture are sufficient, the crystalline product recovered in step (d) above will tend to contain significant quantities oof the precursor in addition to the AEI/CHA intergrowth. On calcination to remove the organic directing agent from the pores of the intergrowth, the precursor is at least partly dehydrated to produce one or more impurity phases, such as one or more of phosphocristobolite, phosphotridymite, ALPO-A, ALPO-C, ALPO-D, ALPO-E, dehydrated variscite and dehydrated metavariscite. Surprisingly, however, when the crystalline product comprisng the AEI/CHA intergrowth and the impurity phase is used in a catalyst composition for the conversion of oxygenates to olefins, it is found that the catalyst composition retains excellent selectivity to ethylene and propylene, particularly when the impurity phase is present in an amount up to 40%, for example between about 3% and about 30%, for example between about 5% and about 15%, by weight of the total weight of said at least one intergrown phase and said impurity phase.

It is also found that the crystalline product can contain up to 0.75% of an AFI framework type impurity phase by weight of the AEI/CHA intergrowth, in addition to the intergrowth and the (silico)aluminophosphate hydrate precursor, without significantly reducing its selectivity to ethylene and propylene when used as an oxygenate conversion catalyst.

Before use in the process of the invention, the crystalline product will normally be formulated into a catalyst composition by combination with other materials, such as binders and/or matrix materials, which provide additional hardness or catalytic activity to the finished catalyst.

Materials which can be blended with the intergrown crystalline material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product ranges from 10 to 90 weight percent of the total catalyst, preferably 20 to 80 weight percent of the total catalyst.

As previously stated, the catalyst composition of the invention is particularly intended for use in the conversion of oxygenates to olefins. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is (are) generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

Using the various oxygenate feedstocks discussed above, particularly a feedstock containing methanol, the catalyst composition of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The resultant olefins can be separated from the oxygenate conversion product for sale or can be fed to a downstream process for converting the olefins to, for example, polymers.

The invention will now be more particularly described with reference to the following Examples.

In the examples, DIFFaX analysis was used to determine the AEI/CHA ratio of the molecular sieves. Simulated powder XRD diffraction patterns for varying ratios of AEI/CHA were generated using the DIFFaX program available from the International Zeolite Association (see also M. M. J. Tracey et al., Proceedings of the Royal Chemical Society, London, A (1991), Vol. 433, pp. 499-520 "Collection of Simulated XRD Powder Patterns for Zeolites" by M. M. J. Treacy and J. B. Higgins, 2001, Fourth Edition, published on behalf of the Structure Commission of the International Zeolite Association). The DIFFaX input file used to simulate the XRD diffraction patterns is given in Table 2 of U.S. Patent Application Publication No. 2002/0165089, incorporated herein by reference. In order to obtain best fitting between the DIFFaX simulated patterns and the experimental patterns, two sets of simulated XRD patterns were generated using a line broadening of 0.009 (as described in U.S. Patent Application No. 2002/0165089) and a line broadening of 0.04 (FIGS. 1a and 1b). The simulated diffraction patterns were then compared with the experimental powder XRD diffraction patterns. In this respect, a very sensitive range is the 15 to 19.5 2θ range.

EXAMPLE 1

A mixture of 191.86 g of phosphoric acid (85% in water), 187.19 g of demineralized water and 350.33 g of tetraethylammonium hydroxide solution (35% in water, Sachem) was prepared in a mixer bowl and, after initiating stirring of the mixture, 12.47 g Ludox AS 40 (40% silica) was added to the mixer bowl followed by 113.23 g of alumina (Condea Pural SB-1). The composition of the final synthesis mixture in terms of molar ratios was as follows:

0.10SiO$_2$/Al$_2$O$_3$/P$_2$O$_5$/TEAOH/35 H$_2$O

The mixture was transferred to a stainless steel autoclave and heated at 25° C./hour to 150° C. while stirring. The autoclave was kept at 150° C. for 72 hours, it being appreciated that conventional EMM-2 preparations with a crystallization time of 72 hours would tend to employ a synthesis temperature of at least 165° C. After cooling to room temperature, the slurry was washed and dried and an X-ray diffraction pattern of the crystalline product was taken after the calcination procedure described above. Using this diffraction pattern, DIFFaX analysis was conducted and showed the crystalline product to contain a single AEI/CHA intergrowth having an AEI/CHA ratio of 20/80 together with an APC framework type impurity phase.

EXAMPLE 2 (COMPARATIVE)

The procedure of Example 1 was repeated but with the autoclave being heated at 22.5° C./hour to 150° C. with stirring and then being retained at this temperature for only 9 hours before being allowed to cool. In this case, X-ray diffraction analysis showed the crystalline product to consist substantially entirely of an APC framework type material, with no AEI/CHA intergrowth being detected. Similar results were obtained when the synthesis time was increased to 12 hours.

EXAMPLES 3 TO 5

The procedure of Example 1 was repeated at varying heating rates and with the autoclave being retained under stirring at 150° C. for various times. The results are summarized in Table 2, where EMM-2 designates a single AEI/CHA intergrowth having an AEI/CHA ratio of 5/95 to 40/60 as determined by DIFFaX analysis.

TABLE 2

| Example | Heat Rate ° C./hr | Heat Time hrs | Product XRD | AEI/CHA |
|---|---|---|---|---|
| 3 | 25 | 72 | EMM-2 + APC | 14/86 |
| 4 | 22.5 | 96* | EMM-2 + APC | |
| 5 | 22.5 | 96* | EMM-2 + APC | |

*In Examples 4 and 5, a representative example was taken and analyzed after 12 hrs at 150° C., while the rest of the mixture was re-heated to 150° C. under similar conditions for an additional 60 hrs. Then a 2nd sample was taken and analyzed and the rest of the mixture was heated to 150° C. for an additional 24 hrs. The bulk of the mixture had therefore been heated at 150° C. for 96 hrs.

EXAMPLE 6

The calcined products produced in Examples 1 and 3 to 5 were evaluated for MTO performance in a fixed bed reactor, equipped with on-line gas chromatography, at 450° C., 25 WHSV and 25 psig (273 kPa) methanol partial pressure. The weighed averages (selectivities) of the effluent samples were calculated based on the following formula:

$(x_1)(y_1)+(x_2-x_1)(y_2)+(x_3-x_2)(y_2+y_3)/2+(x_4-x_3)(y_3+y_4)/2+\ldots,$ where $y_i$ and $x_i$ are yield and g methanol fed/g sieve, respectively.

The results are summarized in Table 3, where POS means the total weighted averaged selectivities of ethylene and propylene and $C_3^°$ is the weighted average selectivity of propane in the product. Catalyst Life (g/g catalyst) reported is methanol that was cumulatively converted. MTO activity was measured at 450° C., 500 WHSV and 9 psig (98 kPa) methanol partial pressure and is expressed as $k_{max}$, where $k_{max}$ is the first order rate constant calculated at maximum methanol conversion according to the following equation:

$k_{max}(Hz)=-\ln(1-X_{max})/\tau$ where $X_{max}$ is the maximum methanol conversion, and $\tau$ is space time(sec).

$K_{max}$ values are also shown in Table 3.

TABLE 3

| Catalyst Example | MeOH Conv. % | POS | C$_3$O Wt % | k$_{max}$ | Catalyst Life g MeOH/g sieve |
|---|---|---|---|---|---|
| 1 | 15.3 | 75.7 | 1.4 | 667 | 11.4 |
| 3 | 15.2 | 74.3 | 2.3 | 529 | 13.7 |
| 4 | 14.9 | 75.2 | 1.2 | N.A | 11.7 |
| 5 | 13.9 | 74.3 | 1.6 | N.A | 9.6 |

N.A = not available

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for converting an oxygenate-containing feedstock to a product comprising olefins, the process comprising contacting the feedstock under oxygenate to olefin conversion conditions with a catalyst comprising a first crystalline silicoaluminophosphate molecular sieve comprising at least one intergrown form of an AEI structure type material and a CHA structure type material, and a second crystalline material different from said first molecular sieve and resulting from dehydration of an aluminophosphate or silicoaluminophosphate hydrate.

2. The process of claim 1, wherein the oxygenate-containing feedstock comprises methanol, dimethyl ether, or mixtures thereof and the product comprises ethylene and propylene.

3. The process of claim 1 and further comprising converting the olefins to polymer.

* * * * *